US008759383B2

(12) United States Patent
Tung

(10) Patent No.: US 8,759,383 B2
(45) Date of Patent: Jun. 24, 2014

(54) INHIBITORS OF CHOLESTEROL ESTER TRANSFER PROTEIN

(75) Inventor: Roger Tung, Lexington, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 1176 days.

(21) Appl. No.: 12/049,074

(22) Filed: Mar. 14, 2008

(65) Prior Publication Data

US 2008/0242711 A1    Oct. 2, 2008

Related U.S. Application Data

(60) Provisional application No. 60/895,207, filed on Mar. 16, 2007, provisional application No. 61/029,687, filed on Feb. 19, 2008.

(51) Int. Cl.
*A61K 31/421* (2006.01)
*C07D 263/04* (2006.01)

(52) U.S. Cl.
USPC ........... 514/376; 548/215; 548/225; 548/229; 514/374

(58) Field of Classification Search
USPC .................. 548/215, 225, 229; 514/374, 376
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 7,652,049 B2 * | 1/2010 | Ali et al. | 514/376 |
| 2006/0040999 A1 | 2/2006 | Ali et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| WO | 95/26325 A2 | 10/1995 |
| WO | WO 2006/014413 | 2/2006 |
| WO | WO 2007/005572 | 1/2007 |
| WO | 2007/118651 A1 | 10/2007 |

OTHER PUBLICATIONS

Ali et al (2006): STN International HCAPLUS database, (Columbus, Ohio), Accession number: 2006:117052.*
Anet, F et al., Convenient preparation of perdeuterated cyclooctene: effect of inhibitors on catalytic exchange. Tetrahedron Letters 1970; 11(11):829-32.
Fisher, M.B. et al., The complexities inherent in attempts to decrease drug clearance by blocking sites of CYP-mediated metabolism. Curr Opin Drug Discov Devel. Jan. 2006;9(1):101-9.
Kushner, D.J. et al., Pharmacological uses and perspectives of heavy water and deuterated compounds. Can J Physiol Pharmacol. Feb. 1999;77(2):79-88.

Baillie, T.A., "The use of stable isotopes in pharmacological research". Pharmacol Rev. (1981) vol. 33(2), pp. 81-132.
Browne, T.R., "Stable isotope techniques in early drug development: an economic evaluation". J Clin Pharmacol. (1998), vol. 38(3), pp. 213-220.
Cherrah, Y. et al., "Study of deuterium isotope effects on protein binding by gas chromatography/mass spectrometry. Caffeine and deuterated isotopomers". Biomedical and Environmental Mass Spectrometry (1987), vol. 14(11), pp. 653-657.
Dyck, L.E. et al., "Effects of deuterium substitution on the catabolism of beta-phenylethylamine: an in vivo study". J. Neurochem. (1986), vol. 46(2), pp. 399-404.
Foster, A.B., "Deuterium isotope effects in studies of drug metabolism". Trends Pharm Sci. (1984), vol. 5, pp. 524-527.
Foster, A.B., "Deuterium isotope effects in the metabolism of drugs and xenobiotics: implications for drug design". Advances in Drug Research (1985), vol. 14, pp. 1-40.
Gouyette, A., "Synthesis of deuterium-labelled elliptinium and its use in metabolic studies". Biomedical and Environmental Mass Spectrometry. (1988) vol. 15(5), pp. 243-247.
Haskins N. J., "The application of stable isotopes in biomedical research". Biomed Mass Spectrom. (1982) vol. 9(7), pp. 269-277.
Honma, S. et al., "The metabolism of roxatidine acetate hydrochloride. Liberation of deuterium from the piperidine ring during hydroxylation". Drug Metab Dispos. (1987), vol. 15(4), pp. 551-559.
Kumar, S. et al., "Metabolism and excretion of anacetrapib, a novel inhibitor of the cholesteryl ester transfer protein, in humans". Drug Metab. Dispos., (2010), vol. 38(3), pp. 474-483.
Park, B.K. et al., "Metabolism of fluorine-containing drugs". Annu. Rev. Pharmacol. Toxicol. (2001), vol. 41, pp. 443-470.
Pieniaszek, H.J. Jr. et al., "Moricizine bioavailability via simultaneous, dual, stable isotope administration: bioequivalence implications". J Clin Pharmacol. (1999), vol. 39(8), pp. 817-825.
Tan, E.Y. et al., "Pharmacokinetics, metabolism, and excretion of anacetrapib, a novel inhibitor of the cholesteryl ester transfer protein, in rats and rhesus monkeys". Drug Metab. Dispos., (2010) vol. 38(3), pp. 459-473.
Tonn, G.R. et al., "Simultaneous analysis of diphenhydramine and a stable isotope analog (2H10)diphenhydramine using capillary gas chromatography with mass selective detection in biological fluids from chronically instrumented pregnant ewes". Biological Mass Spectrometry (1993) vol. 22, pp. 633-642.
Wolen, R.L., "The application of stable isotopes to studies of drug bioavailability and bioequivalence". J Clin Pharmacol. (1986), vol. 26(6), pp. 419-424.

* cited by examiner

*Primary Examiner* — Golam M M Shameem
(74) *Attorney, Agent, or Firm* — Hamilton, Brook, Smith & Reynolds, P.C.

(57) ABSTRACT

The invention relates to novel oxazolidinones their derivatives, pharmaceutically acceptable salts, solvates, and hydrates thereof. This invention also provides compositions comprising a compound of this invention and the use of such compositions in methods of treating diseases and conditions that are beneficially treated by administering cholesterol ester transfer protein inhibitors.

15 Claims, No Drawings

INHIBITORS OF CHOLESTEROL ESTER TRANSFER PROTEIN

CROSS REFERENCE TO RELATED APPLICATIONS

This application claims priority to U.S. Application No. 60/895,207, filed Mar. 16, 2007, and 61/029,687, filed Feb. 19, 2008, which are incorporated herein by reference in their entirety.

FIELD OF THE INVENTION

This invention relates to novel oxazolidinones their derivatives, pharmaceutically acceptable salts, solvates, and hydrates thereof. This invention also provides compositions comprising a compound of this invention and the use of such compositions in methods of treating diseases and conditions that are beneficially treated by administering cholesterol ester transfer protein inhibitors.

BACKGROUND OF THE INVENTION

Anacetrapib also known as 2-oxazolidinone, 5-[3,5-bis(trifluoromethyl)phenyl]-3-[[4'-fluoro-2'-methoxy-5'-(1-methylethyl)-4-(trifluoromethyl)[1,1'-biphenyl]-2-yl]methyl]-4-methyl-, (4S,5R)—; (4S,5R)-5-[3,5-bis(trifluoromethyl)phenyl]-3-{[4'-fluoro-2'-methoxy-5'-(propan-2-yl)-4-(trifluoromethyl)[1,1'-biphenyl]-2-yl]methyl}-4-methyl-1,3-oxazolidin-2-one; and MK-0859 modulates cholesterol ester transfer protein activity.

Anacetrapib is currently in Phase II clinical trials in the United States for the treatment of dyslipidemia (hypercholesterolemia or mixed hyperlipidemia). Anacetrapib is suggested to be useful in the treatment and prevention of coronary heart disease, atherosclerosis, hypertension, diabetes and obesity.

Despite the beneficial activities of anacetrapib, there is a continuing need for new compounds to treat the aforementioned diseases and conditions.

SUMMARY OF THE INVENTION

The invention provides a compound of Formula I:

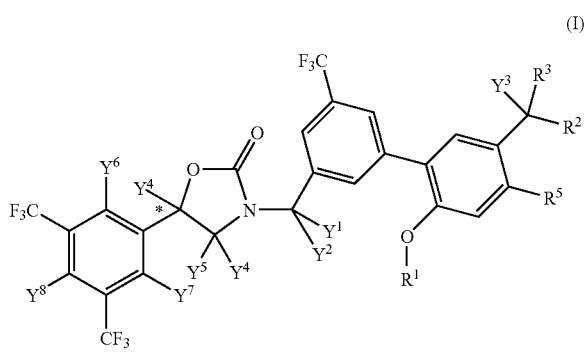

(I)

or a pharmaceutically acceptable salt thereof, wherein each Y is independently selected from hydrogen and deuterium, each of $R^1$, $R^2$, and $R^3$ is independently selected from $CH_3$, $CH_2D$, $CHD_2$, and $CD_3$, $R^4$ is selected from H, $CH_3$, $CH_2D$, $CHD_2$, and $CD_3$, $R^5$ is selected from H and F, and the stereochemistry at * is either (R) or (S), wherein when each of $R^1$, $R^2$, and $R^3$ is $CH_3$, and $R^4$ is selected from H and $CH_3$, then at least one Y is deuterium.

In an embodiment of the invention, $R^1$ is $CD_3$, $R^4$ is selected from H and $CH_3$, —$CY^3(R^2)(R^3)$ is selected from —$CH(CH_3)_2$, —$CD(CD_3)_2$, —$CD(CH_2D)CH_3$, and $Y^4$, $Y^5$, $Y^6$, $Y^7$ and $Y^8$ are simultaneously hydrogen.

In another embodiment of the invention, wherein $R^1$ is $CD_3$, $R^4$ is selected from H and $CH_3$, —$CY^3(R^2)(R^3)$ is selected from —$CH(CH_3)_2$, —$CD(CD_3)_2$, —$CD(CH_2D)CH_3$, and $Y^4$, $Y^5$, $Y^6$, $Y^7$ and $Y^8$ are simultaneously hydrogen, $R^4$ is (S)—$CH_3$, $R^5$ is F, $Y^1$ and $Y^2$ are the same, the stereochemistry at * is (R), and the compound is selected from the group of compounds set forth in the table below:

| Cmpd # | $Y^1$ and $Y^2$ | $Y^3$ | $R^2$ | $R^3$ |
|---|---|---|---|---|
| 101 | H | H | $CH_3$ | $CH_3$ |
| 110 | D | H | $CH_3$ | $CH_3$ |
| 117 | H | D | $CH_2D$ | $CH_3$ |
| 125 | H | D | $CD_3$ | $CD_3$ |
| 158 | H | D | $CH_3$ | $CH_3$ |
| 159 | D | D | $CH_3$ | $CH_3$ |
| 160 | D | D | $CD_3$ | $CD_3$ |
| 161 | H | H | $CD_3$ | $CD_3$ |
| 162 | D | H | $CD_3$ | $CD_3$ |

The invention also provides a compound of Formula II:

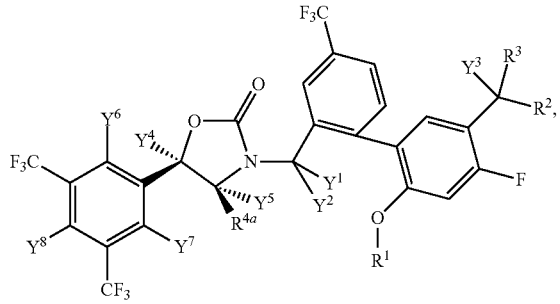

(II)

or a pharmaceutically acceptable salt thereof, wherein each Y is independently selected from hydrogen and deuterium, and each R is independently selected from $CH_3$, $CH_2D$, $CHD_2$, and $CD_3$, wherein, when each of R is $CH_3$, at least one Y is deuterium.

In an embodiment of the invention, in the compound of Formula II, each R is independently selected from $CH_3$ and $CD_3$. In another compound of Formula II, $R^1$ is $CD_3$. Further embodiments include compounds of Formula II in which $R^2$ and $R^3$ are the same, and/or $R^{4a}$ is $CH_3$, and/or $Y^1$ and $Y^2$ are the same, and/or $Y^4$ and $Y^5$ are the same, and/or $Y^6$, $Y^7$, and $Y^8$ are the same.

In certain embodiments, the invention provides a compound of Formula II, selected from the group of compounds wherein $Y^1$, $Y^2$, $Y^3$, $Y^4$, $Y^5$, $R^1$, $R^2$, $R^3$, and $R^4$ are as set forth in the table below:

| Cmpd | $Y^1$ and $Y^2$ | $Y^3$ | $Y^4$ and $Y^5$ | $R^1$ | $R^2$ and $R^3$ | $R^{4a}$ |
|---|---|---|---|---|---|---|
| 163 | H | H | H | $CH_3$ | $CD_3$ | $CH_3$ |
| 164 | H | D | H | $CH_3$ | $CD_3$ | $CH_3$ |
| 165 | D | H | H | $CH_3$ | $CD_3$ | $CH_3$ |

| Cmpd | Y¹ and Y² | Y³ | Y⁴ and Y⁵ | R¹ | R² and R³ | R⁴ᵃ |
|---|---|---|---|---|---|---|
| 166 | D | D | H | CH₃ | CD₃ | CH₃ |
| 167 | H | H | H | CH₃ | CD₃ | CD₃ |
| 168 | H | D | H | CH₃ | CD₃ | CD₃ |
| 169 | D | H | H | CH₃ | CD₃ | CD₃ |
| 170 | D | D | H | CH₃ | CD₃ | CD₃ |
| 171 | H | H | H | CH₃ | CH₃ | CD₃ |
| 172 | H | D | H | CH₃ | CH₃ | CD₃ |
| 173 | D | H | H | CH₃ | CH₃ | CD₃ |
| 174 | D | D | H | CH₃ | CH₃ | CD₃ |
| 175 | H | D | H | CH₃ | CH₃ | CH₃ |
| 176 | D | H | H | CH₃ | CH₃ | CH₃ |
| 177 | D | D | H | CH₃ | CH₃ | CH₃ |
| 178 | H | H | H | CD₃ | CH₃ | CH₃ |
| 179 | H | D | H | CD₃ | CD₃ | CD₃ |
| 180 | D | H | H | CD₃ | CD₃ | CD₃ |
| 181 | D | D | H | CD₃ | CD₃ | CD₃ |
| 182 | H | H | H | CD₃ | CH₃ | CD₃ |
| 183 | H | D | H | CD₃ | CH₃ | CD₃ |
| 184 | D | H | H | CD₃ | CH₃ | CD₃ |
| 185 | D | D | H | CD₃ | CH₃ | CD₃ |
| 186 | H | H | D | CH₃ | CD₃ | CH₃ |
| 187 | H | D | D | CH₃ | CD₃ | CH₃ |
| 188 | D | H | D | CH₃ | CD₃ | CH₃ |
| 189 | D | D | D | CH₃ | CD₃ | CH₃ |
| 190 | H | H | D | CH₃ | CD₃ | CD₃ |
| 191 | H | D | D | CH₃ | CD₃ | CD₃ |
| 192 | D | H | D | CH₃ | CD₃ | CD₃ |
| 193 | D | D | D | CH₃ | CD₃ | CD₃ |
| 194 | H | H | D | CH₃ | CH₃ | CD₃ |
| 195 | H | D | D | CH₃ | CH₃ | CD₃ |
| 196 | D | H | D | CH₃ | CH₃ | CD₃ |
| 197 | D | D | D | CH₃ | CH₃ | CD₃ |
| 198 | H | H | D | CH₃ | CH₃ | CH₃ |
| 199 | D | H | D | CH₃ | CH₃ | CH₃ |
| 200 | D | D | D | CH₃ | CH₃ | CH₃ |
| 201 | H | H | D | CD₃ | CD₃ | CD₃ |
| 202 | H | D | D | CD₃ | CD₃ | CD₃ |
| 203 | D | H | D | CD₃ | CD₃ | CD₃ |
| 204 | D | D | D | CD₃ | CD₃ | CD₃ |
| 205 | H | H | D | CD₃ | CH₃ | CD₃ |
| 206 | H | D | D | CD₃ | CH₃ | CD₃ |
| 207 | D | H | D | CD₃ | CH₃ | CD₃ |
| 208 | D | D | D | CD₃ | CH₃ | CD₃ |

In certain embodiments, the compound of Formula II is selected from:

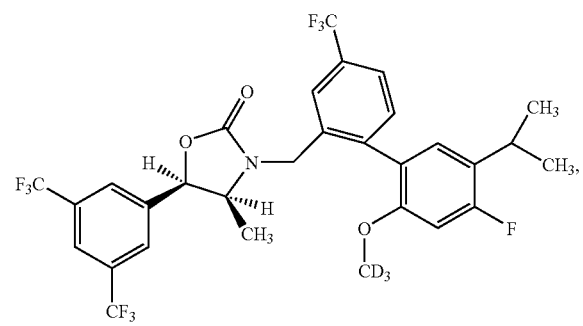

Compound 101

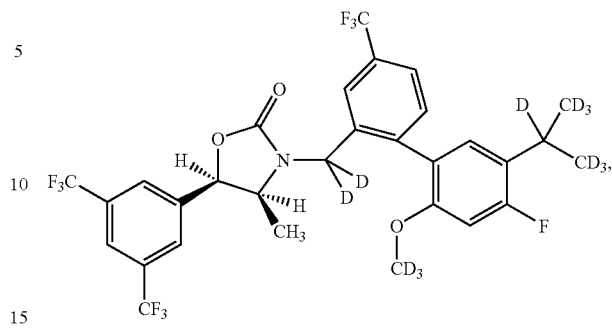

Compound 160

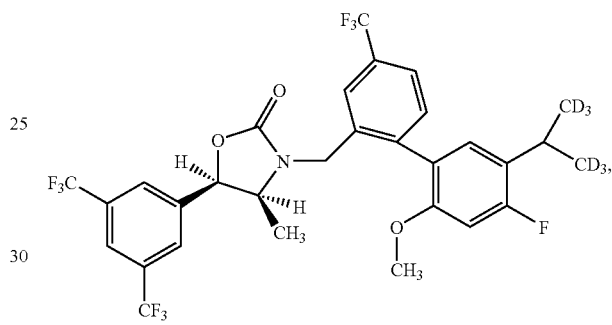

Compound 163

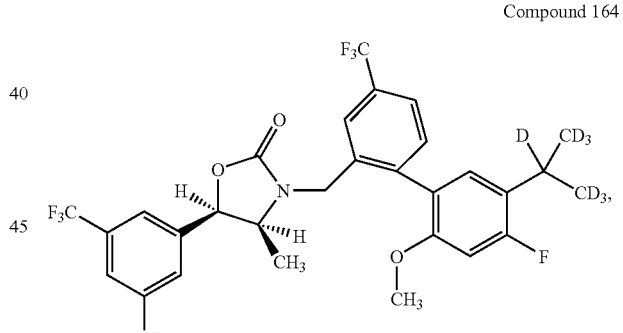

Compound 164

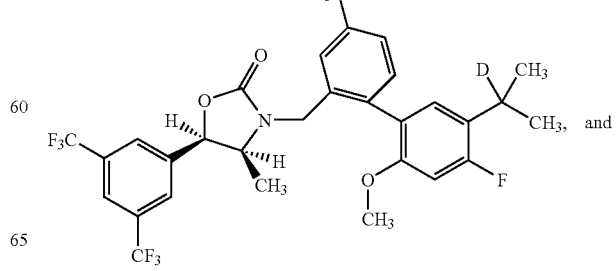

Compound 175, and

-continued

Compound 176

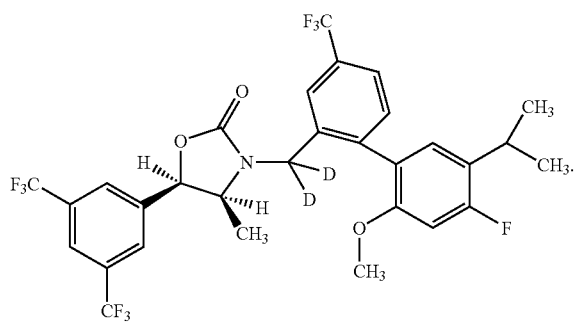

In compounds of the invention, any atom not designated as deuterium is present at its natural isotopic abundance.

The invention further provides a pyrogen-free composition comprising a compound of Formula I or Formula II and an acceptable carrier. In such a composition formulated for pharmaceutical administration, the carrier is a pharmaceutically acceptable carrier.

In an embodiment of the invention, the composition further comprises a second therapeutic agent useful in the treatment or prevention of a disease or condition selected from arteriosclerosis, atherosclerosis, peripheral vascular disease, dyslipidemia, obesity, hypertension, diabetes, and angina. Such second therapeutic agents include, but are not limited to, an HMG CoA reductase inhibitor, a calcium channel blocker, an angiotensin A-II antagonist, an angiotensin converting inhibitor, an alpha-adrenergic blockers, a beta-adrenergic blockers, a diuretic, and a cannabinoid CB1 antagonist. In one embodiment, the second therapeutic agent is atorvastatin.

The invention provides a method of modulating the activity of cholesterol ester transfer protein in a cell, comprising contacting the cell with a compound of Formula I or Formula II.

The invention also provides a method of treating a patient suffering from or susceptible to a disease or condition selected from hypercholesterolemia, arteriosclerosis, atherosclerosis, peripheral vascular disease, hyperlipidemia, dyslipidemia, obesity, hypertension, diabetes, and angina comprising the step of administering to the patient a composition comprising a compound of Formula I or Formula II and an acceptable carrier. In an embodiment of the invention, the patient is suffering from or susceptible to dyslipidemia According to the invention, a compound of Formula I or Formula II may be adminstered with a second therapeutic agent useful in the treatment or prevention of a disease or condition selected from arteriosclerosis, atherosclerosis, peripheral vascular disease, dyslipidemia, obesity, hypertension, diabetes, and angina. In an embodiment of the invention, the second therapeutic agent is selected from an HMG CoA reductase inhibitor, a calcium channel blocker, an angiotensin A-II antagonist, an angiotensin converting inhibitor, an alpha-adrenergic blockers, a beta-adrenergic blockers, a diuretic, and a cannabinoid CB1 antagonist. In an embodiment of the invention, the second therapeutic agent is atorvastatin and the patient is suffering from or susceptible to dyslipidemia.

DETAILED DESCRIPTION OF THE INVENTION

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of anacetrapib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E. et al., Seikagaku 1994, 66:15; Ganes, L. Z. et al., Comp. Biochem. Physiol. Mol. Integr. Physiol. 1998, 119:725. In a compound of this invention, when a particular position is designated as having deuterium, it is understood that the abundance of deuterium at that position is substantially greater than the natural abundance of deuterium, which is 0.015%. A position designated as having deuterium has a minimum isotopic enrichment factor of at least about 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least about 3500 (52.5% deuterium incorporation at each designated deuterium atom), at least about 4000 (60% deuterium incorporation), at least about 4500 (67.5% deuterium incorporation), at least about 5000 (75% deuterium incorporation), at least about 5500 (82.5% deuterium incorporation), at least about 6000 (90% deuterium incorporation), at least about 6333.3 (95% deuterium incorporation), at least about 6466.7 (97% deuterium incorporation), at least about 6600 (99% deuterium incorporation), or at least about 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen," the position is understood to have hydrogen at its natural abundance isotopic composition.

The term "isotopologue" refers to a species that differs from a specific compound of this invention only in the isotopic composition thereof.

The term "compound," as used herein, is also intended to include any salts, solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable" as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfate, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I or II), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than 1% of other stereoisomers are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

Both "$^2$H" and "D" refer to deuterium.

"Stereoisomer" refers to both enantiomers and diastereomers.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

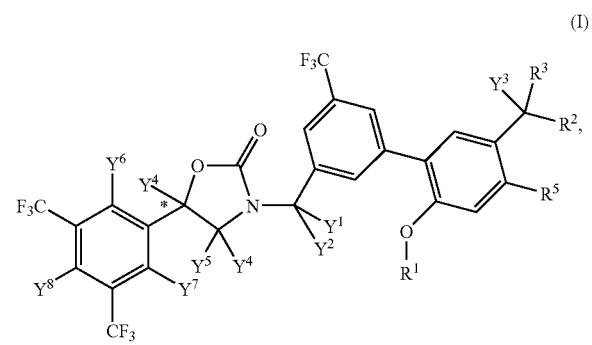

(I)

or a salt, hydrate or solvate thereof, wherein:

each Y is independently selected from hydrogen and deuterium;

each of $R^1$, $R^2$, and $R^3$ is independently selected from $CH_3$, $CH_2D$, $CHD_2$, and $CD_3$;

$R^4$ is selected from H, $CH_3$, $CH_2D$, $CHD_2$, and $CD_3$;

$R^5$ is selected from H and F;

The stereochemistry at "*" is (S) or (R); and wherein, when each of $R^1$, $R^2$, and $R^3$ is $CH_3$, and $R^4$ is selected from H and $CH_3$, then at least one Y is deuterium.

In certain embodiments of a compound of Formula I $R^1$ is $CD_3$, $R^4$ is selected from H and $CH_3$; —$CY^3(R^2)(R^3)$ is selected from —$CH(CH_3)_2$, —$CD(CD_3)_2$, —$CD(CH_2D)$ $CH_3$; and $Y^4, Y^5, Y^6, Y^7$ and $Y^8$ are simultaneously hydrogen.

In yet another embodiment, the compound is a compound of Formula I, wherein $R^1$ is $CD_3$; $R^4$ is (S)—$CH_3$; $R^5$ is F; $Y^1$ and $Y^2$ are the same; the stereochemistry at * is (R); $Y^4, Y^5, Y^6, Y^7$ and $Y^8$ are simultaneously hydrogen; and the compound is selected from any one of the compounds (Cmpd) set forth in Table 1.

TABLE 1

Exemplary Embodiments of Formula I

| Cmpd # | $Y^1$ and $Y^2$ | $Y^3$ | $R^2$ | $R^3$ |
|---|---|---|---|---|
| 101 | H | H | $CH_3$ | $CH_3$ |
| 110 | D | H | $CH_3$ | $CH_3$ |
| 117 | H | D | $CH_2D$ | $CH_3$ |
| 125 | H | D | $CD_3$ | $CD_3$ |
| 158 | H | D | $CH_3$ | $CH_3$ |
| 159 | D | D | $CH_3$ | $CH_3$ |
| 160 | D | D | $CD_3$ | $CD_3$ |
| 161 | H | H | $CD_3$ | $CD_3$ |
| 162 | D | H | $CD_3$ | $CD_3$ |

In other embodiments, the invention provides a compound of Formula II:

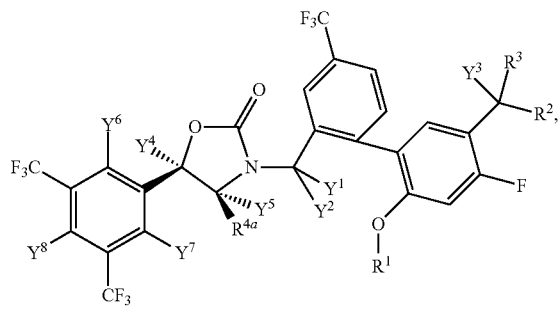

(II)

or a salt, hydrate or solvate thereof, wherein:
each Y is independently selected from hydrogen and deuterium; and
each of R is independently selected from $CH_3$, $CH_2D$, $CHD_2$, and $CD_3$;
wherein, when each of R is $CH_3$, at least one Y is deuterium.

In certain embodiments of formula II:
a) each R is independently selected from $CH_3$ and $CD_3$;
b) $R^1$ is $CD_3$;
c) $R^2$ and $R^3$ are the same;
d) $R^{4a}$ is $CH_3$;
e) $Y^1$ and $Y^2$ are the same;
f) $Y^4$ and $Y^5$ are the same; or
g) $Y^6$, $Y^7$ and $Y^8$ are the same.

In more specific embodiments, the compound of Formula I has the features set forth in at least two of a) through g).

In yet another embodiment, the compound is a compound of Formula II, wherein $R^2$ and $R^3$ are the same; $Y^1$ and $Y^2$ are the same; $Y^4$ and $Y^5$ are the same; $Y^6$, $Y^7$ and $Y^8$ are simultaneously hydrogen; and the compound is selected from any one of the compounds (Cmpd) set forth in Table 2.

TABLE 2

Exemplary Embodiments of Formula II

| Cmpd | $Y^1$ and $Y^2$ | $Y^3$ | $Y^4$ and $Y^5$ | $R^1$ | $R^2$ and $R^3$ | $R^{4a}$ |
|---|---|---|---|---|---|---|
| 163 | H | H | H | $CH_3$ | $CD_3$ | $CH_3$ |
| 164 | H | D | H | $CH_3$ | $CD_3$ | $CH_3$ |
| 165 | D | H | H | $CH_3$ | $CD_3$ | $CH_3$ |
| 166 | D | D | H | $CH_3$ | $CD_3$ | $CH_3$ |
| 167 | H | H | H | $CH_3$ | $CD_3$ | $CD_3$ |
| 168 | H | D | H | $CH_3$ | $CD_3$ | $CD_3$ |
| 169 | D | H | H | $CH_3$ | $CD_3$ | $CD_3$ |
| 170 | D | D | H | $CH_3$ | $CD_3$ | $CD_3$ |
| 171 | H | H | H | $CH_3$ | $CH_3$ | $CD_3$ |
| 172 | H | D | H | $CH_3$ | $CH_3$ | $CD_3$ |
| 173 | D | H | H | $CH_3$ | $CH_3$ | $CD_3$ |
| 174 | D | D | H | $CH_3$ | $CH_3$ | $CD_3$ |
| 175 | H | D | H | $CH_3$ | $CH_3$ | $CH_3$ |
| 176 | D | H | H | $CH_3$ | $CH_3$ | $CH_3$ |
| 177 | D | D | H | $CH_3$ | $CH_3$ | $CH_3$ |
| 178 | H | H | H | $CD_3$ | $CD_3$ | $CD_3$ |
| 179 | H | D | H | $CD_3$ | $CD_3$ | $CD_3$ |
| 180 | D | H | H | $CD_3$ | $CD_3$ | $CD_3$ |
| 181 | D | D | H | $CD_3$ | $CD_3$ | $CD_3$ |
| 182 | H | H | H | $CD_3$ | $CH_3$ | $CD_3$ |
| 183 | H | D | H | $CD_3$ | $CH_3$ | $CD_3$ |
| 184 | D | H | H | $CD_3$ | $CH_3$ | $CD_3$ |
| 185 | D | D | H | $CD_3$ | $CH_3$ | $CD_3$ |
| 186 | H | H | D | $CD_3$ | $CH_3$ | $CD_3$ |
| 187 | H | D | D | $CD_3$ | $CH_3$ | $CD_3$ |
| 188 | D | H | D | $CH_3$ | $CH_3$ | $CD_3$ |
| 189 | D | D | D | $CH_3$ | $CH_3$ | $CD_3$ |
| 190 | H | H | D | $CH_3$ | $CD_3$ | $CD_3$ |
| 191 | H | D | D | $CH_3$ | $CD_3$ | $CD_3$ |

TABLE 2-continued

Exemplary Embodiments of Formula II

| Cmpd | $Y^1$ and $Y^2$ | $Y^3$ | $Y^4$ and $Y^5$ | $R^1$ | $R^2$ and $R^3$ | $R^{4a}$ |
|---|---|---|---|---|---|---|
| 192 | D | H | D | $CH_3$ | $CD_3$ | $CD_3$ |
| 193 | D | D | D | $CH_3$ | $CD_3$ | $CD_3$ |
| 194 | H | H | D | $CH_3$ | $CH_3$ | $CD_3$ |
| 195 | H | D | D | $CH_3$ | $CH_3$ | $CD_3$ |
| 196 | D | H | D | $CH_3$ | $CH_3$ | $CD_3$ |
| 197 | D | D | D | $CH_3$ | $CH_3$ | $CD_3$ |
| 198 | H | D | D | $CH_3$ | $CH_3$ | $CH_3$ |
| 199 | D | H | D | $CH_3$ | $CH_3$ | $CH_3$ |
| 200 | D | D | D | $CH_3$ | $CH_3$ | $CH_3$ |
| 201 | H | H | D | $CD_3$ | $CD_3$ | $CD_3$ |
| 202 | H | D | D | $CD_3$ | $CD_3$ | $CD_3$ |
| 203 | D | H | D | $CD_3$ | $CD_3$ | $CD_3$ |
| 204 | D | D | D | $CD_3$ | $CD_3$ | $CD_3$ |
| 205 | H | H | D | $CD_3$ | $CH_3$ | $CD_3$ |
| 206 | H | D | D | $CD_3$ | $CH_3$ | $CD_3$ |
| 207 | D | H | D | $CD_3$ | $CH_3$ | $CD_3$ |
| 208 | D | D | D | $CD_3$ | $CH_3$ | $CD_3$ |

It will be apparent that Compounds Nos. 101, 110, 125, 158, 159, 160, 161 and 162 from Table 1 are also compounds of Formula II and have been omitted from Table 2 for the sake of clarity and to avoid redundancy.

In a more specific embodiment, the compound of this invention is selected from:

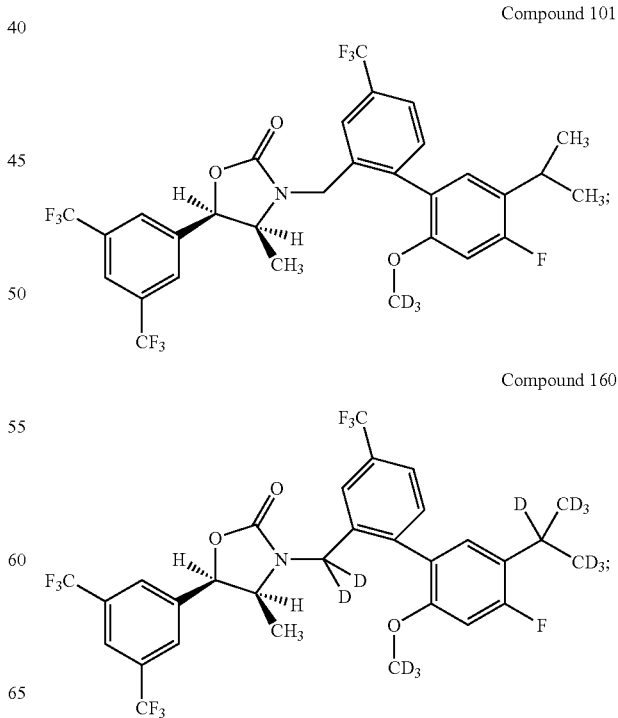

-continued

Compound 163

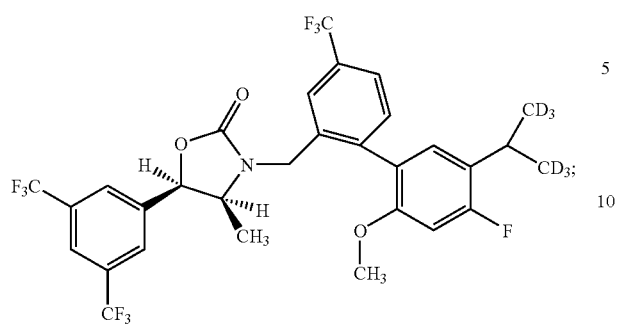

Compound 164

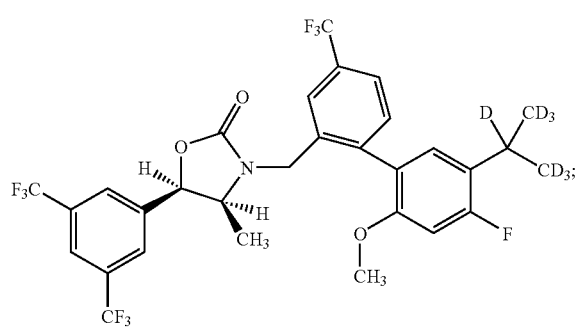

Compound 175

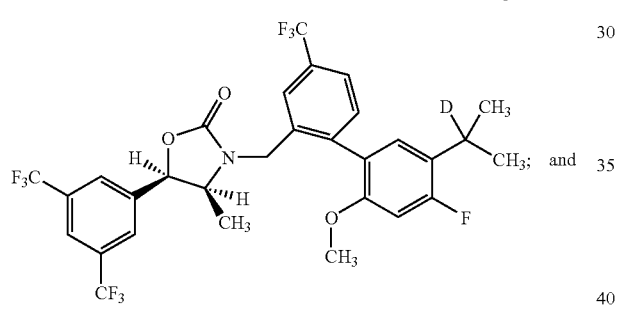

Compound 176

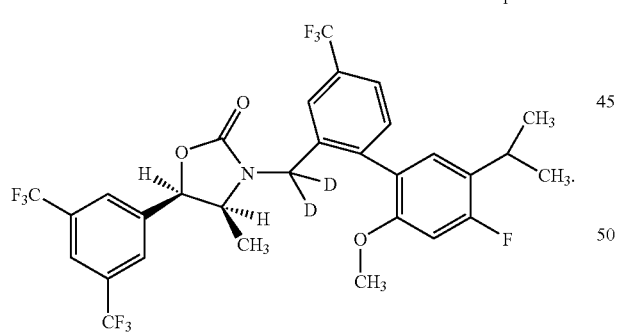

In another set of embodiments, any atom not designated as deuterium in any of the embodiments set forth above is present at its natural isotopic abundance.

The synthesis of compounds of Formulae I and II can be readily achieved by synthetic chemists of ordinary skill. Relevant procedures and intermediates are disclosed, for instance in U.S. Patent Application 2006/0040999 and in PCT publication WO2007/005572.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I or II is depicted in Scheme 1.

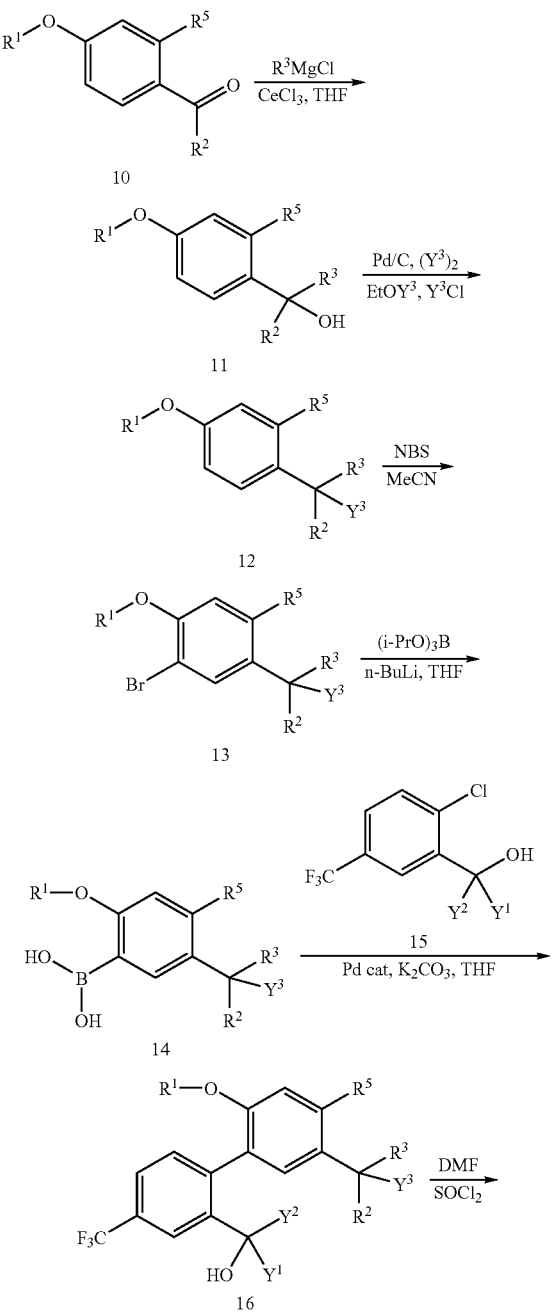

Scheme 1.

13

-continued

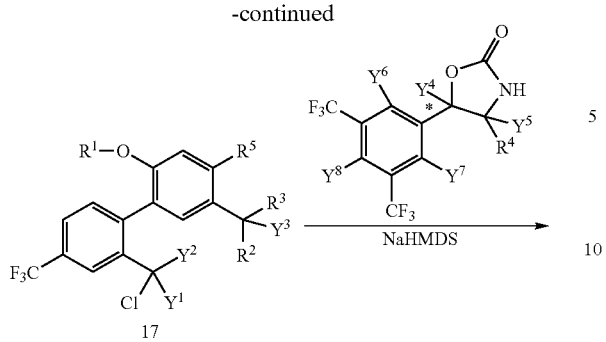

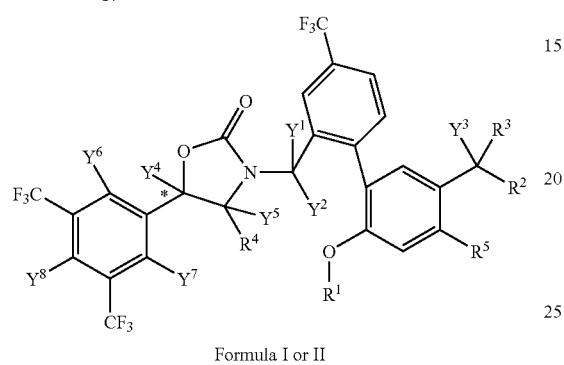

Formula I or II

An appropriately deuterated 1-(4-hydroxyphenyl)ethanone 10 is reduced to the corresponding alcohol 11 using an appropriately deuterated methyl magnesium chloride and $CeCl_3$. The alcohol 11 is hydrogenated to the anisole 12 over a palladium/carbon catalyst in the presence of hydrogen or deuterium gas. The anisole 12 is then brominated with NBS to produce aryl bromide 13, which is then converted to boronic acid intermediate 14 by treatment with tri-isopropylborate. The boronic acid 14 is then coupled with an appropriately deuterated (2-chloro-5-(trifluoromethyl)phenyl)methanol 15 using a Suzuki coupling reaction to produce biaryl intermediate 16. The biaryl intermediate is chlorinated with thionyl chloride to produce intermediate 17. Intermediate 17 is then alkylated with oxazolidinone reagent 18 to yield a compound of Formula I or II.

The synthesis of oxazolidinone reagent 18 is shown in Scheme 2.

Scheme 2.

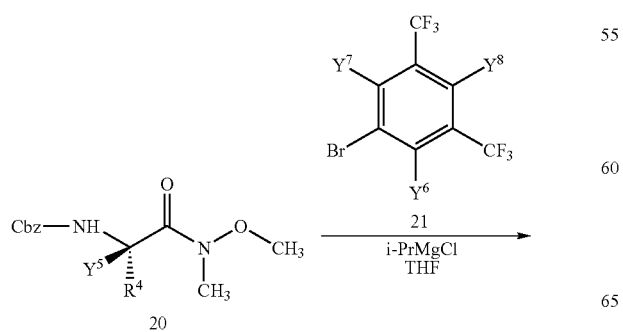

14

-continued

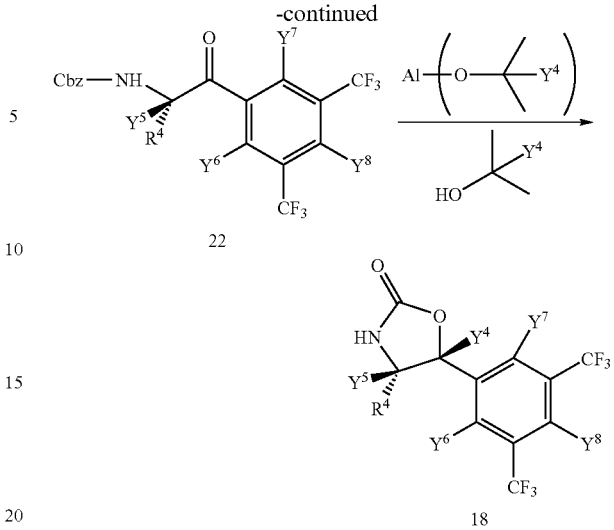

The Weinreb amide 20 is synthesized from commercially available CBZ-L-alanine or CBZ-L-glycine (the enantiomer of 20 is obtained by using commercially available CBZ-D-alanine or CBZ-D-glycine), HOBT-hydrate and Weinreb amine HCl salt as described in PCT publication WO2007005572. The amide 20 is combined with 3,5-bis (trifluoromethyl)bromobenzene 21 to produce ketone 22, which is then reduced to the chiral oxazolidinone reagent 18 using $Al(O-i-Pr)_3$, as described in PCT publication WO2007005572. Incorporation of deuterium for $Y^4$ can be accomplished by performing the Meerwein-Ponndorf-Verley reaction using deuterated reagents as disclosed by Williams, E D et al, JACS 1953, 75:2404-2407.

An appropriately deuterated 1-(4-hydroxyphenyl)ethanone 10 is produced according to Scheme 3.

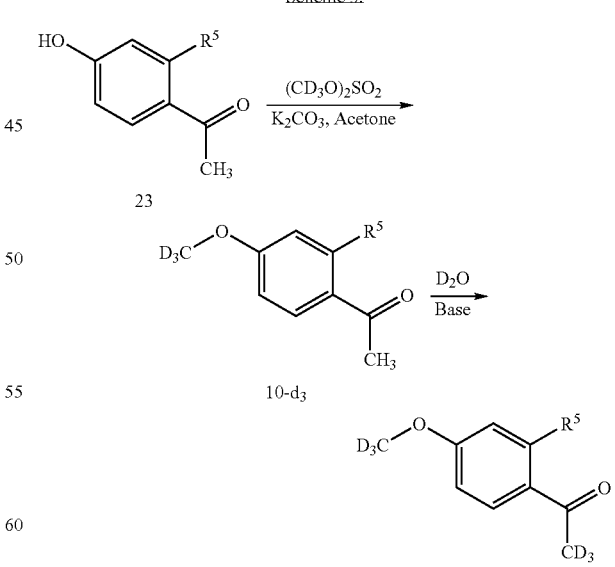

1-(4-hydroxyphenyl)ethanone 23 or 1-(2-fluoro-4-hydroxyphenyl)ethanone 23 is deuteromethylated by reaction with $d_6$-dimethyl sulfate and potassium carbonate in acetone to produce the corresponding 1-(4-d$_3$-methoxyphenyl)etha-none 10-d$_3$, which may be further deuterated with D$_2$O in base to form the corresponding 1-(4-d$_3$-methoxyphenyl)-d$_3$-ethanone 10-d$_6$.

An appropriately deuterated (2-chloro-5-(trifluoromethyl) phenyl)methanol 15 can be produced from the corresponding acid 30 by one of Schemes 4A or 4B.

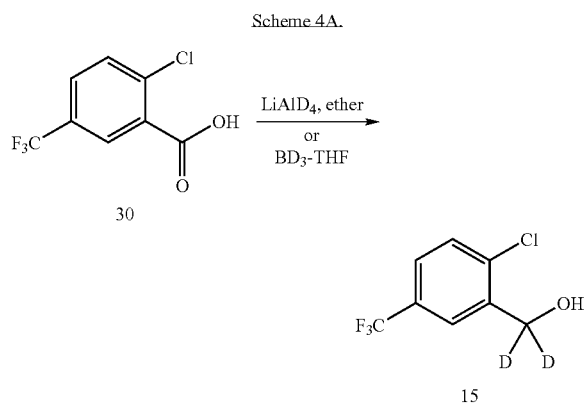

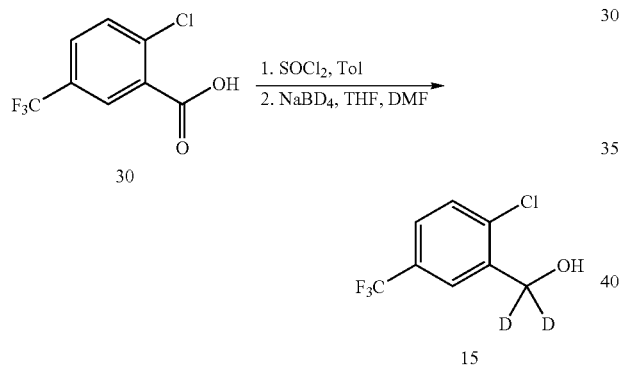

In Scheme 4A, 2-chloro-5-(trifluoromethyl)benzoic acid 30 is reduced with lithium aluminum deuteride in ether or BD$_3$-THF to produce (2-chloro-5-(trifluoromethyl)phenyl)-d$_2$-methanol 11 using the procedure disclosed in Angew Chemie Intl Ed 2007, 46(10):1719-1722; or Bioorg Med Chem 2006, 14(22):7625-7651.

In Scheme 4B, 2-chloro-5-(trifluoromethyl)benzoic acid 30 is treated with sulfonyl chloride in toluene, followed by reduction with sodium borodeuteride in THF and DMF to produce (2-chloro-5-(trifluoromethyl)phenyl)-d$_2$-methanol 11 using the procedure disclosed in Org Lett 2007, 9(14): 2649-2651.

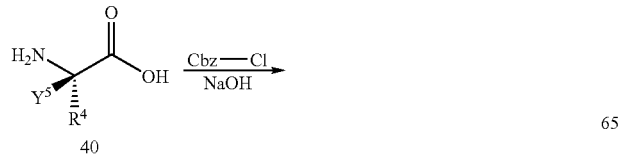

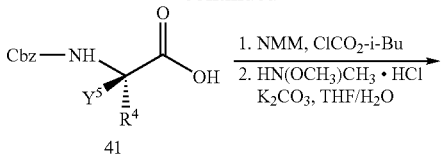

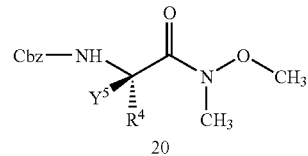

In Scheme 5, a synthetic route to deuterated analogs of compound 20 is shown. Commercially available deuterated analogs of L-Alanine (40) are reacted with benzyl chloroformate under Shotten-Bauman conditions to provide 41 as described by Aitken, R A et al, J Chem Soc Perk Trans 2002, 1:533-541. The acid can then be converted to the deuterated analogs of Weinreb Amide 20 as described by Kano, S et al, Chem Pharm Bull 1988, 36(9):3296-3303.

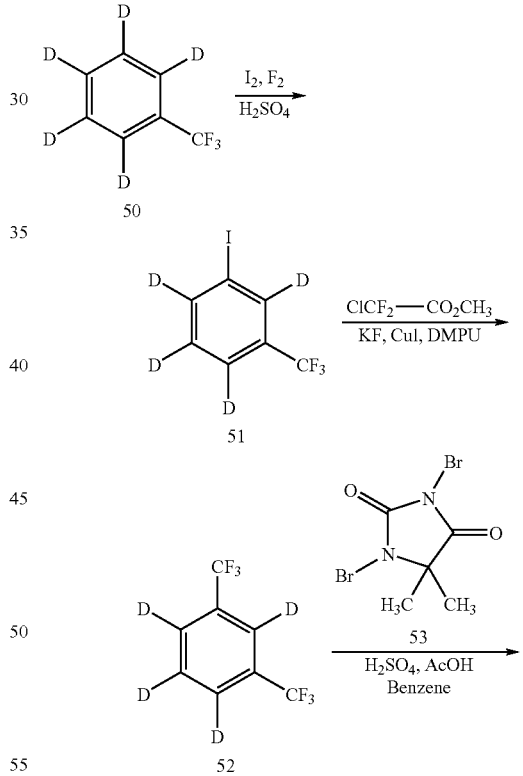

In Scheme 6, a synthetic route to deuterated analogs of compound 21 is shown. Commercially available d5-trifluoromethylbenzene (50) can be regioselectively iodinated to provide 51 in high yields according to the method of Chambers, R D et al, J Chem Soc Chem Comm 1995, 1:19. The iodine substituent can be readily converted to the trifluoromethyl 52 according to the procedure of MacNeil, J G et al, J Fluorine Chem 1991, 55(2):225-227. The deuterated analog of 21 can be obtained by selective bromination according to the method of Leazer, J L et al, J Org Chem 2003, 68(9): 3695-3698.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are those that result in the formation of stable compounds.

Compounds of formula I are inhibitors of cholesteryl ester transfer protein (CETP), a plasma protein that facilitates the transfer of cholesterol ester from high-density lipoprotein (HDL) to low density lipoprotein (LDL) and very low density lipoprotein (VLDL). Various methods are known in the art for confirming activity of CETP inhibitors, and assay kits for determination of CETP activity and inhibition, in vitro or ex vivo, are commercially available. For example, the CETP Inhibitor Drug Screening Kit (BioVision Research Products, Mountain View, Calif.) can be used to assay inhibitors directly. An assay for measuring CETP inhibition in plasma is available from Roar Biomedical, Inc. (New York, N.Y.).

Compositions

The invention also provides pyrogen-free compositions comprising an effective amount of a compound of Formula I or II (e.g., including any of the formulae herein), or a pharmaceutically acceptable salt, solvate, or hydrate of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 2006/0094744 and 2006/0079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as anacetrapib. Such agents include those indicated as being useful in combination with anacetrapib, including but not limited to, those described in U.S. Pat. No. 6,197,786; and U.S. Patent Applications 2006/0270675; 2007/0004774; 2006/0178514; and 2006/0040999.

Preferably, the second therapeutic agent is an agent useful in the treatment of a patient suffering from or susceptible to a disease or condition selected from arteriosclerosis, atherosclerosis, peripheral vascular disease, dyslipidemia and conditions commonly co-morbid with these disease states, including but not limited to, obesity, hypertension, diabetes, and angina. Agents for use in such compositions include an HMG CoA reductase inhibitor, including but not limited to lovastatin, simvastatin, pravastatin, fluindostatin, venostatin, dihydrocompactin, compactin, fluvastatin, atorvastatin, glenvastatin, dalvastatin, cerivastatin, crilvastatin, bervastatin, cerivastatin, rosuvastatin, pitavastatin, mevastatin, or rivastatin. Other agents for combination therapy include antihypertensive agents, including calcium channel blockers (including but not limited to felodipine, nifedipine or amlodipine), angiotensin A-II antagonists (including but not limited to losartan, irbesartan, telmisartan or valsartan), angiotensin converting inhibitors (including but not limited to benazepril, captopril, enalapril, fosinopril, lisinopril, perindopril, quinapril, trandolapril, ramipril, zestril, zofenopril, cilazapril, temocapril, spirapril, moexipril, delapril, imidapril, ramipril, terazosin, urapidil, indoramin, amosulalol, and alfuzosin), alpha-adrenergic blockers, (including but not limited to doxazosin, prazosin and trimazosin), beta-adrenergic blockers (including but not limited to carvedilol), diuretics (including but not limited to amiloride, bendroflumethiazide, and hydrochlorothiazide), cannabinoid CB1 antagonists including but not limited to rimonabant), and pharmaceutically acceptable salts, hydrates, solvates, and/or polymorphs of the foregoing. Combinations, compositions, and methods of use relevant to compounds of this invention are described in a number of patents and patent applications including, but not limited to, U.S. Pat. No. 6,197,786; and U.S. Patent Applications 2006/0270675; 2007/0004774; 2006/0178514; and 2006/0040999. Each of the patents, patent applications, and publications, whether in traditional journals or available only through the internet, referred to herein, is incorporated in its entirety by reference.

In one embodiment, the second therapeutic agent is atorvastatin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from 0.1 mg to 3000 mg/day. In another embodiment, an effective amount of a compound of this invention can range from 1 mg to 300 mg/day. In still another embodiment, an effective amount of a compound of this invention can range from 10 mg to 300 mg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for anacetrapib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that combinations with second therapeutic agents referenced above will provide improved therapeutic responses. For example, cholesterol levels can be reduced relative to a monotherapy. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, additive or synergistic improvements in efficacy, improved ease of administration or use and/or reduced overall expense of compound preparation or formulation.

Methods of Treatment

In another embodiment, the invention provides a method of modulating the activity of cholesterol ester transfer protein in a cell, comprising contacting a cell with one or more compounds of Formula I or II herein.

According to another embodiment, the invention provides a method of treating a patient suffering from, or susceptible to, a disease that is beneficially treated by anacetrapib comprising the step of administering to said patient an effective amount of a compound or a composition of this invention. Such diseases are well known in the art and include, but are not limited to, high cholesterol, arteriosclerosis, peripheral vascular disease, hyperlipidemia, dyslipidemia, obesity, hypertension, diabetes, and angina. See, e.g., U.S. patent publications 2006/0270675; 2007/0004774; 2006/0178514; and 2006/0040999.

In one particular embodiment, the method of this invention is used to treat a patient suffering from or susceptible to dyslipidemia (hypercholesterolemia and mixed hyperlipidemia).

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with anacetrapib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or II and atorvastatin for treatment of dyslipidemia.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or II alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I or II for use in the treatment or prevention in a patient of a disease, disorder or symptom thereof delineated herein.

Diagnostic Methods and Kits

The compounds and compositions of this invention are also useful as reagents in methods for determining the concentration of anacetrapib in solution or biological sample such as plasma, examining the metabolism of anacetrapib and other analytical studies.

According to one embodiment, the invention provides a method of determining the concentration, in a solution or a biological sample, of anacetrapib, comprising the steps of:

a) adding a known concentration of a compound of Formula I or II to the solution of biological sample;

b) subjecting the solution or biological sample to a measuring device that distinguishes anacetrapib from a compound of Formula I or II;

c) calibrating the measuring device to correlate the detected quantity of the compound of Formula I or II with the known concentration of the compound of Formula I or II added to the biological sample or solution; and d) measuring the quantity of anacetrapib in the biological sample with said calibrated measuring device; and e) determining the concentration of anacetrapib in the solution of sample using the correlation between detected quantity and concentration obtained for a compound of Formula I or II.

Measuring devices that can distinguish anacetrapib from the corresponding compound of Formula I or II include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I or II comprising the steps of contacting the compound of Formula I or II with a metabolizing enzyme source for a period of time and comparing the amount of the compound of Formula I or II with the metabolic products of the compound of Formula I or II after the period of time.

In a related embodiment, the invention provides a method of evaluating the metabolic stability of a compound of Formula I or II in a patient following administration of the compound of Formula I or II. This method comprises the steps of obtaining a serum, urine or feces sample from the patient at a period of time following the administration of the compound of Formula I or II to the subject; and comparing the amount of the compound of Formula I or II with the metabolic products of the compound of Formula I or II in the serum, urine or feces sample.

The present invention also provides kits for use to treat. These kits comprise (a) a pharmaceutical composition comprising a compound of Formula I or II or a salt, hydrate, or solvate thereof, wherein said pharmaceutical composition is in a container; and (b) instructions describing a method of using the pharmaceutical composition to treat.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (4S,5R)-5-(3,5-bis(trifluoromethyl)phenyl)-3-((4'-fluoro-5'-(1,1,1,2,3,3,3-d$_7$)isopropyl-2'-methoxy-4-(trifluoromethyl)biphenyl-2-yl)methyl)-4-methyl-1,3-oxazolidin-2-one (Compound 164)

The synthesis of (4S,5R)-5-(3,5-bis(trifluoromethyl)phenyl)-3-((4'-fluoro-5'-(1,1,1,2,3,3,3-d$_7$)isopropyl-2'-methoxy-4-(trifluoromethyl)biphenyl-2-yl)methyl)-4-methyl-1,3-oxazolidin-2-one (Compound 164) was carried out according to the procedure outlined in Scheme 7 below.

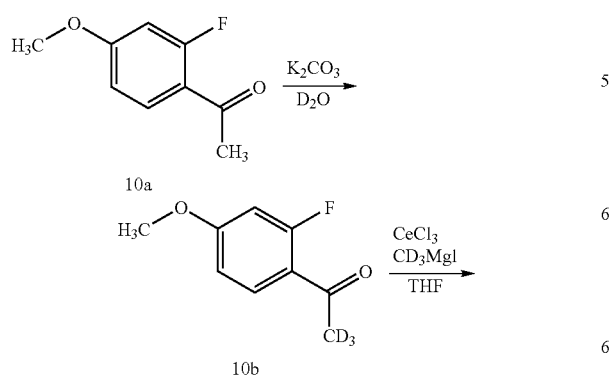

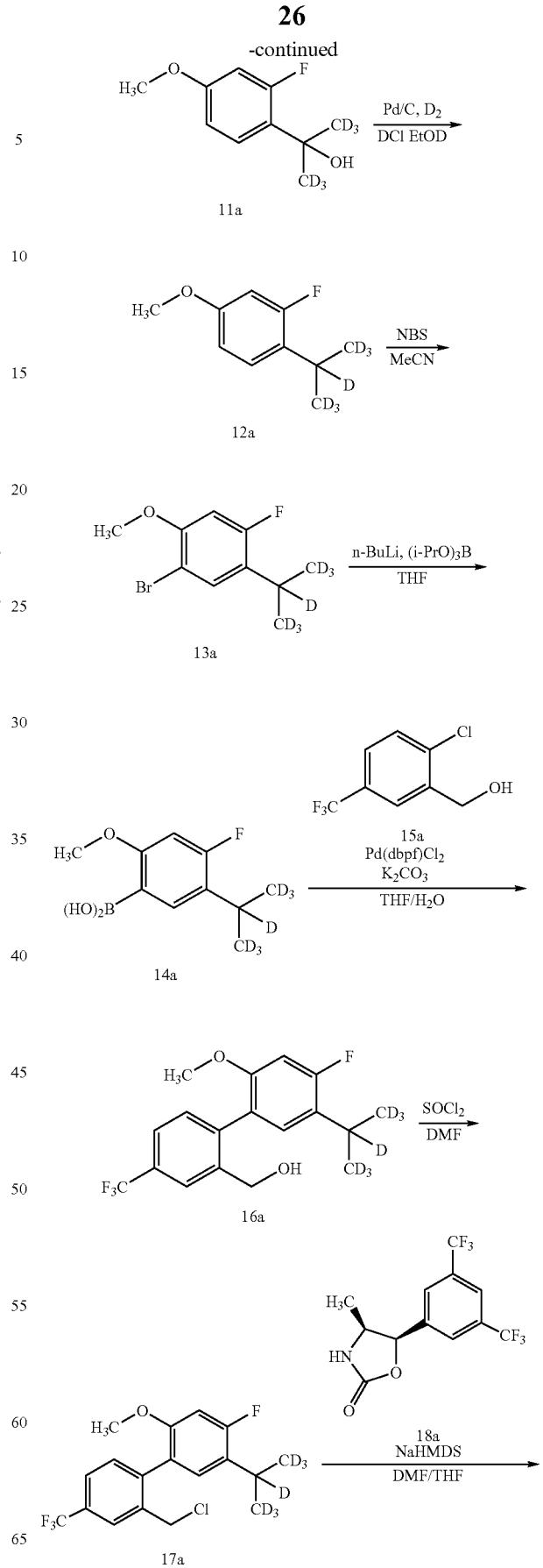

-continued

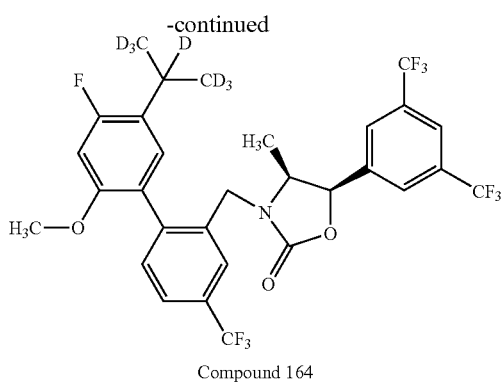

Compound 164

Synthesis of 1-(2-fluoro-4-methoxyphenyl)-(2,2,2-d₃)ethanone (10b)

A mixture of 2-fluoro-4-methoxyacetophenone 10a (65 g), K₂CO₃ (117 g), D₂O (100 mL), MeOD (50 mL) and THF (60 mL) was stirred at 60-65° C. for 15 hours (hr). The reaction mixture was cooled and diluted with MTBE (800 mL). The organic phase was washed with water (100 mL×2), then brine, dried (Na₂SO₄), filtered and the solvent removed under reduced pressure. The crude product obtained was again subjected to the H/D exchange conditions above. Following the same workup procedure above the organic solution was concentrated under reduced pressure to ~100 mL, heptanes were added in small portions until a saturated solution was obtained and the resulting mixture was allowed to stand overnight. The resulting solids were filtered and dried to give approximately 35 g of 10b. A 2$^{nd}$ crop (16 g) was obtained from the mother liquor. ¹H NMR (CDCl₃) δ: 7.91 (t, 1H), 6.75 (dd, 1H), 6.60 (dd, 1H), 3.88 (s, 3H).

Synthesis of 2-(2-fluoro-4-methoxyphenyl)-(1,1,1,3,3,3-d₆)propan-2-ol (11a)

CeCl₃ (10.8 g) was stirred in THF (120 mL) overnight (approximately 15 hr). The mixture was cooled to <–8° C. and 1M CD₃MgI in THF (44 mL) was added dropwise at <–5° C. The reaction mixture was stirred for 2 hr at <–5° C. A solution of 10b (6 g) in THF (70 mL) was added dropwise at <0° C. When addition was complete, the mixture was stirred 1 hr at <0° C. A 3M HCl solution (70 mL) was added slowly to quench the reaction, then water (100 mL) and EtOAc (500 mL) were added. The mixture was transferred to a separatory funnel, any solids remaining in the reaction flask were washed with EtOAc (100 mL), the EtOAc washing was added to the separatory funnel, and the solids were discarded. The phases were separated and the aqueous phase was extracted with EtOAc (100 mL×2). The combined organic solution was washed with water, sat'd NaHCO₃ solution (2×), brine, dried (Na₂SO₄), filtered and the solvent removed under reduced pressure. The crude product was purified by chromatography on silica gel to give 5.2 g (86%) of 11a as a pale yellow oil. [Note: High purity of 11a is required for use in the next reaction step.] ¹H NMR (CDCl₃) δ 7.42 (t, 1H), 6.7-6.65 (dd, 1H), 6.62-6.58 (dd, 1H), 3.77 (s, 3H), 2.08 (d, 1H); MS m/z=173 (M+H–H₂O).

Synthesis of 2-Fluoro-1-(1,1,1,2,3,3,3-d₇)isopropyl-4-methoxybenzene (12a)

A mixture of 11a (800 mg), 10% Pd/C (120 mg), and 34% DCl in D₂O (0.5 mL) in EtOD (4 mL) was shaken under D₂ (15 psi) at 40° C. for 4 hr. The resulting mixture was filtered through a pad of Celite, and the pad washed with MTBE (200 mL). The filtrate was washed with water (30 mL×4), then brine, dried (Na₂SO₄), filtered and the solvent removed under reduced pressure at room temperature [Note: 12a is volatile] to give 800 mg of 12a used directly for the following step without further purification. ¹H NMR (CDCl₃) δ 7.14 (t, 1H), 6.67-6.62 (dd, H), 6.59-6.55 (dd, 1H), 3.77 (s, 3H).

Synthesis of 1-bromo-4-fluoro-5-(1,1,1,2,3,3,3-d₇)isopropyl-2-methoxybenzene (13a)

A solution of 12a (5 g) in MeCN (150 mL) was heated to 30° C. and NBS (5.9 g) was added in one portion. The resulting yellow solution was heated at 30-40° C. for 2 hr. The mixture was cooled to room temperature and diluted with water (30 mL) and aqueous Na₂S₂O₃ solution (20 mL). The mixture was extracted with MTBE (500 mL). The organic phase was washed with brine, dried (Na₂SO₄), filtered and the solvent removed under reduced pressure. The crude product was purified by chromatography on silica gel to give 6.0 g (80%) of 13a. ¹H NMR (CDCl₃) δ 7.37 (d, 1H), 6.60 (d, 1H), 3.83 (s, 3H).

Synthesis of 4-fluoro-5-(1,1,1,2,3,3,3-d₇)isopropyl-2-methoxyphenylboronic acid (14a)

A solution of 13a (6.5 g) and (i-PrO)₃B (8 mL) in THF (50 mL) was cooled to <–70° C. n-BuLi (2.5M in hexanes; 32 mL) was added dropwise via an addition funnel at <–65° C. The reaction was held at –65 to –70° C. for one hr, then raised slowly to –40° C. A solution of 3M H₂SO₄ was added dropwise to quench the reaction and adjust the pH to 1-2. The aqueous phase was extracted with EtOAc (100 mL×2). The combined organic phase was washed with water (2×) and concentrated under reduced pressure to ~20 mL. The mixture was extracted with 1M KOH (10 mL×2). The KOH solution was acidified to pH 1-2. The resulting white solid was collected by filtration and washed with water and heptanes. The wet solid was dried in a vacuum oven for one day at 40-50° C. to give 5.0 g (92%) of 14a.

Synthesis of (4'-fluoro-5'-(1,1,1,2,3,3,3-d₇)isopropyl-2'-methoxy-4-(trifluoromethyl)biphenyl-2-yl)methanol (16a)

A mixture of 14a (3.30 g), (2-chloro-5-(trifluoromethyl)phenyl)methanol (15a) (2.94 g), K₂CO₃ (5.5 g), water (5 mL) and THF (14 mL) was degassed with N₂ for 90 min. Bis(di-t-butylphosphino)ferrocene palladium(II)dichloride (170 mg) was added and the mixture heated at 37-40° C. for 24 hr with vigorous stirring. The reaction mixture was cooled to room temperature, diluted with water (20 mL) and extracted with MTBE (50 mL×3). The combined organic solution was washed with brine, dried (Na₂SO₄), filtered and the solvent removed under reduced pressure. The crude product was purified by chromatography on silica gel to give 4.6 g (88%) of 16a containing a small amount of the corresponding benzaldehyde (via oxidation of the alcohol during reaction). ¹H NMR (CDCl₃) δ 7.95, (s, 1H), 7.6 (d, 1H), 7.28 (d, 1H), 6.98 (d, 1H), 6.69 (d, 1H), 4.59 to 4.38 (m, 2H), 3.75 (s, 3H), 1.99 (t, 1H); MS m/z=332 (M+H–H₂O).

Synthesis of 2'-(chloromethyl)-4-fluoro-5-(1,1,1,2,3,3,3-d$_7$)isopropyl-2-methoxy-4'-(trifluoromethyl)biphenyl (17a)

A solution of 16a (160 mg) in DMF (1 mL) was cooled in an ice bath and thionyl chloride (0.05 mL) added. The reaction mixture was stirred in an ice bath for 0.5 hr, allowed to warm to room temperature and stirred an additional 1 hr. The mixture was quenched with ice and diluted with MTBE (50 mL). The organic phase was washed with water (10 mL), sat'd NaHCO$_3$ solution (10 mL), brine, dried (Na$_2$SO$_4$), filtered and the solvent removed under reduced pressure. The crude product was purified by chromatography on silica gel to give 110 mg (66%) of 17a. $^1$H NMR (CDCl$_3$) δ 7.81 (s, 1H), 7.59 (d, 1H), 7.34 (d, 1H), 7.05 (d, 1H), 6.65 (d, 1H), 4.58-4.30 (broad d, 2H), 3.73 (s, 3H).

Synthesis of (4S,5R)-5-(3,5-bis(trifluoromethyl)phenyl)-3-((4'-fluoro-5'-(1,1,1,2,3,3,3-d$_7$)isopropyl-2'-methoxy-4-(trifluoromethyl)biphenyl-2-yl)methyl)-4-methyl-1,3-oxazolidin-2-one (Compound 164). A solution of (4S,5R)-5-(3,5-bis(trifluoromethyl)phenyl)-4-methyl-1,3-oxazolidin-2-one (18a) [prepared by methods described in WO2007/005572] (112 mg) in DMF (2 mL) was cooled to −20° C. and 1M NaHMDS in THF (0.4 mL) was added slowly, maintaining the reaction temperature at <−15° C. After 5 min, a solution of 17a (110 mg) in DMF (0.5 mL) was added dropwise at <−15° C. The reaction mixture was allowed to warm slowly to 15-16° C. and stirred for 2 hr. The mixture was diluted with MTBE (50 mL) and the solution washed with water (10 mL×2), dilute HCl solution, brine, dried (Na$_2$SO$_4$), filtered and the solvent removed under reduced pressure. The crude product was purified by chromatography on silica gel to give 10 mg of Compound 164. MS m/z=645 (M+H), 667 (M+Na).

Example 2

Synthesis of (4S,5R)-5-(3,5-bis(trifluoromethyl)phenyl)-3-((4'-fluoro-5'-isopropyl-2'-(d$_3$-methoxy)-4-(trifluoromethyl)biphenyl-2-yl)methyl)-4-methyloxazolidin-2-one (Compound 101)

The synthesis of (4S,5R)-5-(3,5-bis(trifluoromethyl)phenyl)-3-((4'-fluoro-5'-isopropyl-2'-(d$_3$-methoxy)-4-(trifluoromethyl)biphenyl-2-yl)methyl)-4-methyloxazolidin-2-one (Compound 101) was carried out as outlined in Scheme 8 below.

Scheme 8.

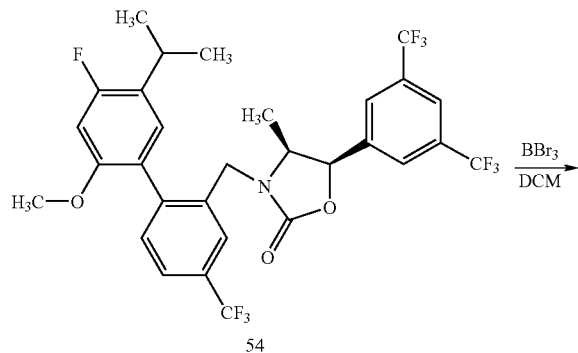

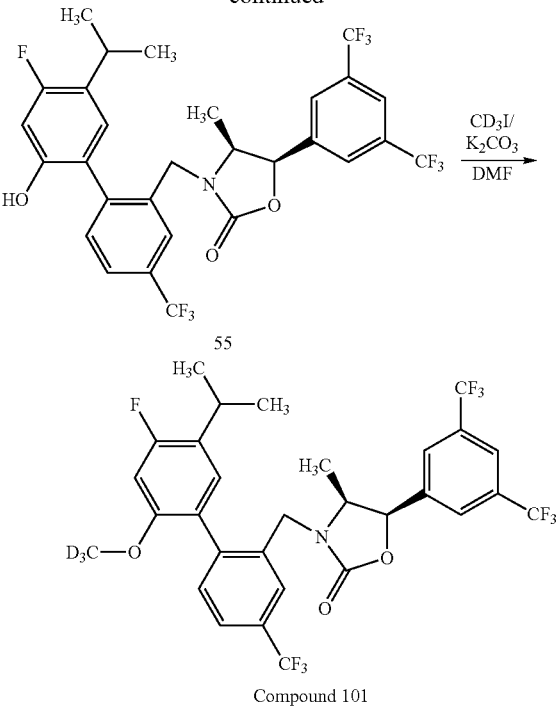

Compound 101

Synthesis of (4S,5R)-5-(3,5-bis(trifluoromethyl)phenyl)-3-((4'-fluoro-5'-isopropyl-2'-hydroxy-4-(trifluoromethyl)biphenyl-2-yl)methyl)-4-methyl-1,3-oxazolidin-2-one (55)

A solution of 4S,5R)-5-(3,5-bis(trifluoromethyl)phenyl)-3-((4'-fluoro-5'-isopropyl-2'-methoxy-4-(trifluoromethyl)biphenyl-2-yl)methyl)-4-methyl-1,3-oxazolidin-2-one (54) [prepared by methods described in WO2007/005572] (1.4 g) in DCM (5 mL) was treated with BBr$_3$ (0.9 mL) at 15-16° C. and the reaction mixture stirred for 1 hr. The mixture was quenched with ice and diluted with EtOAc (150 mL). The mixture was washed with water, sat'd NaHCO$_3$ solution, and brine, dried (Na$_2$SO$_4$), filtered and the solvent concentrated under reduced pressure. The crude product was purified by chromatography on silica gel to give 1.01 g (60%) of 55. $^1$H NMR (CDCl$_3$) δ: 7.85 (s, 1H), 7.75-7.62 (m, 4H), 7.42 (m, 1H), 6.96 (dd, 1H), 7.69 (dd, 1H), 5.64 (d, 0.5H), 5.39 (d, 0.5H), 4.92-4.80 (m, 1H), 4.18 (d, 0.5H), 3.99 (d, 0.5H), 3.85 (m, 0.5H), 3.75 (m, 0.5H), 3.19 (m, 1H), 1.17-1.25 (m, 6H), 0.57 (d, 1.5H), 0.45 (d, 1.5H).

Synthesis of (4S,5R)-5-(3,5-bis(trifluoromethyl)phenyl)-3-((4'-fluoro-5'-isopropyl-2'-(d$_3$-methoxy)-4-(trifluoromethyl)biphenyl-2-yl)methyl)-4-methyl-1,3-oxazolidin-2-one (Compound 101)

To a solution of 55 (1.0 g) in DMF (10 mL) was added iodomethane-d$_3$ (0.3 mL) followed by powdered K$_2$CO$_3$ (0.26 g). The mixture was heated at 50-60° C. for 3 hr then stirred at room temperature overnight. The reaction mixture was diluted with MTBE (200 mL) and the solution washed with water (50 mL×3), brine, dried (Na$_2$SO$_4$), filtered and the solvent concentrated under reduced pressure. The crude product was purified by chromatography on silica gel to give 620 mg (58%) of Compound 101. MS m/z=641(M+H), 663 (M+Na).

Example 3

Synthesis of (4S,5R)-5-(3,5-bis(trifluoromethyl)phenyl)-3-((4'-fluoro-5'-isopropyl-2'-methoxy-4-(trifluoromethyl)biphenyl-2-yl)d₂-methyl)-4-methyl-1,3-oxazolidin-2-one (Compound 176)

The synthesis of (4S,5R)-5-(3,5-bis(trifluoromethyl)phenyl)-3-((4'-fluoro-5'-isopropyl-2'-methoxy-4-(trifluoromethyl)biphenyl-2-yl)d₂-methyl)-4-methyl-1,3-oxazolidin-2-one (Compound 176) was carried out according to the procedure outlined in Scheme 9 below.

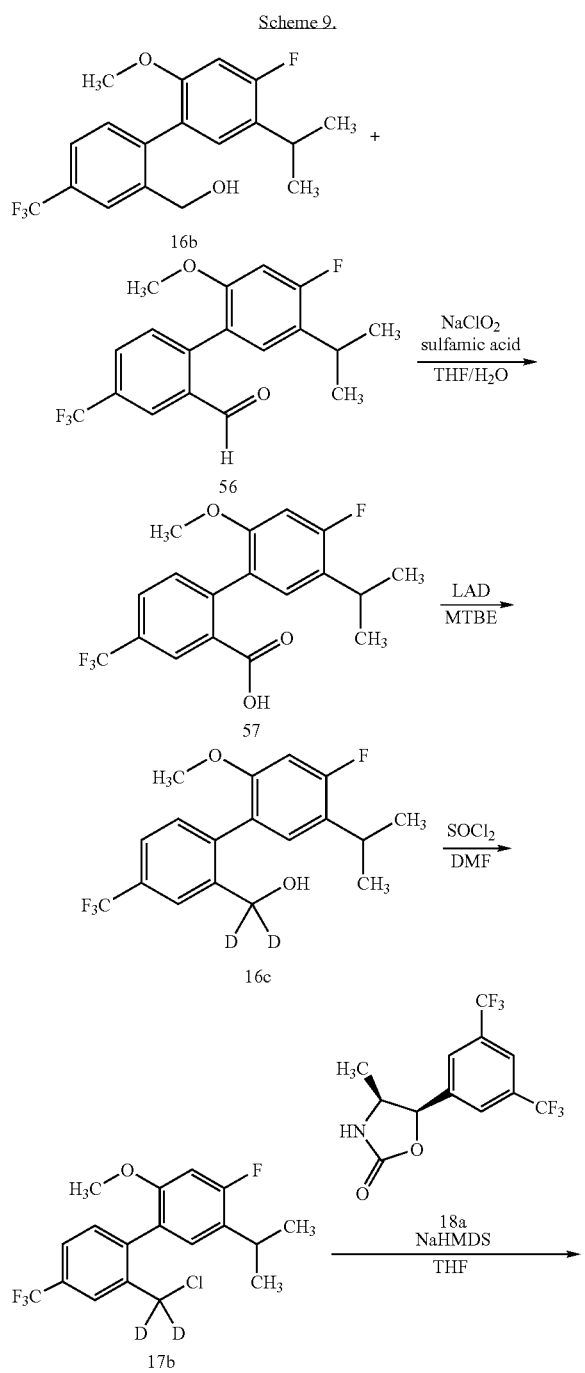

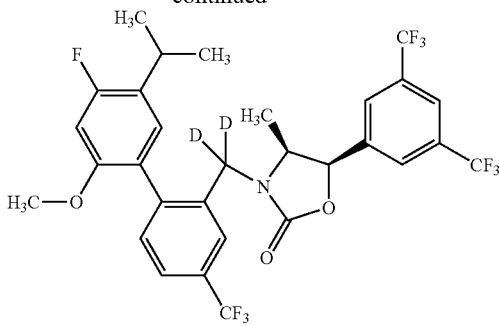

Compound 176

Synthesis of 4'-fluoro-5'-isopropyl-2'-methoxy-4-(trifluoromethyl)biphenyl-2-carboxylic acid (57)

An 8.2 g quantity of a mixture of 4'-fluoro-5'-isopropyl-2'-methoxy-4-(trifluoromethyl)biphenyl-2-yl)methanol 16b and 4'-fluoro-5'-isopropyl-2'-methoxy-4-(trifluoromethyl)biphenyl-2-carbaldehyde 56 [obtained, as a mixture, from a Suzuki coupling by methods described in WO2007/005572] was dissolved along with sulfamic acid (3.3 g) in a mixture of THF (50 mL) and water (50 mL). The solution was cooled in an ice bath. A solution of 80% NaClO₂ (2.6 g) in water (50 mL) was added dropwise from an addition funnel. When addition was complete, the mixture was stirred at <8° C. for 1.5 hr. The mixture was quenched by addition of water and extracted with EtOAc. The organic phase was concentrated under reduced pressure to a volume of 50 mL and extracted with 2N KOH (20 mL×2). The organic phase was reserved. The aqueous solution was acidified to pH 2, and the solid filtered, to yield 300-400 mg of product 57 as a first crop. The reserved organic solution was concentrated under reduced pressure and the resulting crude product purified by chromatography on silica gel to give a total of 1.4-1.5 g of 57.

Synthesis of 4'-fluoro-5'-isopropyl-2'-methoxy-4-(trifluoromethyl)biphenyl-2-yl)d₂-methanol (16c)

A solution of 57 (400 mg) in MTBE (4 mL) was cooled in an ice bath and lithium aluminum deuteride was added in two portions (30 mg and 40 mg). The reaction mixture was allowed to warm to room temperature and was stirred over 3 days. The reaction was quenched with sat'd NH₄Cl solution (20 mL) and the mixture was stirred 20 min. The mixture was filtered and the solid was washed with MTBE (200 mL). The organic solution was washed with water, brine, dried (Na₂SO₄), filtered and the solvent concentrated under reduced pressure. The crude product was combined with an additional batch of crude product obtained from a second reduction of 57 (450 mg scale) and was purified by chromatography on silica gel to give 640 mg of 16c. $^1$H NMR (CDCl₃) δ 7.88 (s, 1H), 7.58 (d, 1H), 7.32 (d, 1H), 7.01 (d, 1H), 6.70 (d, 1H), 3.72 (s, 3H), 3.21 (m, 1H), 2.35 (br, 1H), 1.27 (s, 3H), 1.23 (s, 3H); MS m/z=367 (M+Na).

Synthesis of 2-(d₂-chloromethyl)-4-fluoro-5-isopropyl-2-methoxyl-4'-(trifluoromethyl)biphenyl (17b)

A solution of 16c (640 mg) in DMF (3 mL) was cooled in ice bath and thionyl chloride (0.18 mL) was added. The reaction mixture was stirred in the ice bath for 0.5 hr then allowed to warm to room temperature and stirred an additional 1 hr. The reaction was quenched with ice and diluted with MTBE (200 mL). The organic solution was washed with water (20 mL), sat'd NaHCO₃ solution, brine, dried (Na₂SO₄), filtered and the solvent concentrated under reduced pressure. The crude product was purified by chromatography on silica gel to give 490 mg (80%) of 17b. $^1$H NMR (CDCl₃ δ 7.82 (s, 1H), 7.59 (dd, 1H), 7.34 (d, 1H), 7.07 (d, 1H), 3.72 (s, 3H), 3.20 (m, 1H), 1.24 (s, 3H), 1.20 (s, 3H).

Synthesis of (4S,5R)-5-(3,5-bis(trifluoromethyl)phenyl)-3-((4'-fluoro-5'-isopropyl-2'-methoxy-4-(trifluoromethyl)biphenyl-2-yl)d₂-methyl)-4-methyl-1,3-oxazolidin-2-one (Compound 176). A solution of 18a (495 mg) in DMF (6 mL) was cooled to −20° C. and a 1M solution of NaHMDS in THF (1.7 mL) was added slowly at <−15° C. Five minutes after the addition was complete, a solution of 17b (480 mg) in DMF (3.5 mL) was added dropwise, keeping the temperature at <−15° C. The reaction was allowed to warm slowly to 15-16° C. over 2 hr, and stirred for an additional 2 hr. The reaction mixture was diluted with MTBE (200 mL), washed with water (10 mL×2), dilute HCl, then brine, dried (Na₂SO₄), filtered and the solvent concentrated under reduced pressure to give crude Compound 176. MS m/z=640 (M═H), 662 (M+Na).

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay:

The metabolic stability of compounds of Formula I or II is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures:

Human liver microsomes are obtained from a commercial source (e.g., XenoTech, LLC (Lenexa, Kans.)). The incubation mixtures are prepared as follows:

| Reaction Mixture Composition | |
|---|---|
| Liver Microsomes | 0.5-2.0 mg/mL |
| NADPH | 1 mM |
| Potassium Phosphate, pH 7.4 | 100 mM |
| Magnesium Chloride | 10 mM |
| Test Compound | 0.1-1 µM. |

Incubation of Test Compounds with Liver Microsomes:

The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH₂O to terminate the reaction. The positive controls, testosterone and propranolol, as well as anacetrapib, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay.

Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a compound of Formula I or II in 100 mM potassium phosphate buffer (pH 7.4) was incubated at 37° C. in triplicate. Positive controls contain 1 µM of anacetrapib instead of a compound of Formula I or II. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 µL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:
1. A compound of Formula I:

(I)

[Structure of Formula I]

or a pharmaceutically acceptable salt thereof, wherein:
Each of $Y^1, Y^2, Y^3, Y^4, Y^5, Y^6, Y^7$ and $Y^8$ is independently selected from hydrogen and deuterium;
$R^1$ is $CD_3$;
each of $R^2$ and $R^3$ is independently selected from $CH_3$, $CH_2D$, $CHD_2$, and $CD_3$;
$R^4$ is selected from H, $CH_3$, $CH_2D$, $CHD_2$, and $CD_3$;
$R^5$ is selected from H and F; and
the stereochemistry at * is either (R) or (S).

2. The compound of claim 1, wherein
$R^4$ is selected from H and $CH_3$;
—$CY^3(R^2)(R^3)$ is selected from —$CH(CH_3)_2$, —$CD(CD_3)_2$, and —$CD(CH_2D)CH_3$; and
$Y^4, Y^5, Y^6, Y^7$ and $Y^8$ are simultaneously hydrogen.

3. The compound of claim 2, wherein $R^4$ is (S)—$CH_3$; $R^5$ is F; $Y^1$ and $Y^2$ are the same; the stereochemistry at * is (R); and the compound is selected from any one of the compounds set forth in the table below:

| Cmpd # | $Y^1$ and $Y^2$ | $Y^3$ | $R^2$ | $R^3$ |
|---|---|---|---|---|
| 101 | H | H | $CH_3$ | $CH_3$ |
| 110 | D | H | $CH_3$ | $CH_3$ |
| 117 | H | D | $CH_2D$ | $CH_3$ |
| 125 | H | D | $CD_3$ | $CD_3$ |
| 158 | H | D | $CH_3$ | $CH_3$ |
| 159 | D | D | $CH_3$ | $CH_3$ |
| 160 | D | D | $CD_3$ | $CD_3$ |
| 161 | H | H | $CD_3$ | $CD_3$ |
| 162 | H | D | $CD_3$ | $CD_3$ | or a pharmaceutically acceptable salt thereof.

4. A compound of Formula II:

(II)

[Structure of Formula II]

or a pharmaceutically acceptable salt thereof, wherein:
Each of $Y^1, Y^2, Y^3, Y^4, Y^5, Y^6, Y^7$ and $Y^8$ is independently selected from hydrogen and deuterium;
$R^1$ is $CD_3$; and
each of $R^2$, $R^3$ and $R^{4a}$ is independently selected from $CH_3$ and $CD_3$.

5. The compound of claim 4, wherein $R^2$ and $R^3$ are the same.
6. The compound of claim 4, wherein $R^{4a}$ is $CH_3$.
7. The compound of claim 4, wherein $Y^1$ and $Y^2$ are the same.
8. The compound of claim 4, wherein $Y^4$ and $Y^5$ are the same.
9. The compound of claim 4, wherein $Y^6, Y^7$, and $Y^8$ are the same.
10. The compound of claim 7, wherein $R^2$ and $R^3$ are the same; and the compound is selected from any one of the compounds set forth in the table below:

| Cmpd | $Y^1$ and $Y^2$ | $Y^3$ | $Y^4$ and $Y^5$ | $R^1$ | $R^2$ and $R^3$ | $R^{4a}$ |
|---|---|---|---|---|---|---|
| 178 | H | H | H | $CD_3$ | $CD_3$ | $CD_3$ |
| 179 | H | D | H | $CD_3$ | $CD_3$ | $CD_3$ |
| 180 | D | H | H | $CD_3$ | $CD_3$ | $CD_3$ |
| 181 | D | D | H | $CD_3$ | $CD_3$ | $CD_3$ |
| 182 | H | H | H | $CD_3$ | $CH_3$ | $CD_3$ |
| 183 | H | D | H | $CD_3$ | $CH_3$ | $CD_3$ |
| 184 | D | H | H | $CD_3$ | $CH_3$ | $CD_3$ |
| 185 | D | D | H | $CD_3$ | $CH_3$ | $CD_3$ |
| 201 | H | H | D | $CD_3$ | $CD_3$ | $CD_3$ |
| 202 | H | D | D | $CD_3$ | $CD_3$ | $CD_3$ |
| 203 | D | H | D | $CD_3$ | $CD_3$ | $CD_3$ |
| 204 | D | D | D | $CD_3$ | $CD_3$ | $CD_3$ |
| 205 | H | H | D | $CD_3$ | $CH_3$ | $CD_3$ |
| 206 | H | D | D | $CD_3$ | $CH_3$ | $CD_3$ |
| 207 | D | H | D | $CD_3$ | $CH_3$ | $CD_3$ |
| 208 | D | D | D | $CD_3$ | $CH_3$ | $CD_3$ | and or a pharmaceutically acceptable salt thereof.

11. The compound of claim 4, selected from:

Compound 101

[Structure of Compound 101]

and

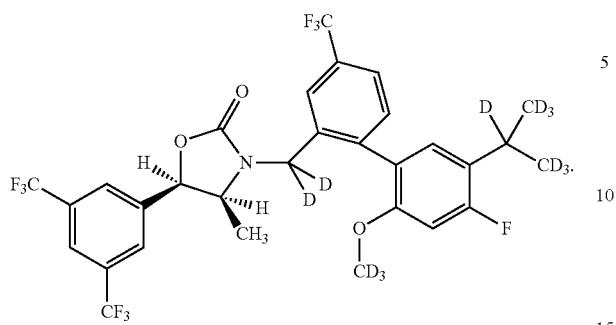

Compound 160

12. The compound of claim 1, wherein any atom not designated as deuterium is present at its natural isotopic abundance.

13. The compound of claim 10, wherein $Y^6$, $Y^7$, and $Y^8$ are simultaneously H.

14. The compound of claim 4, wherein any atom not designated as deuterium is present at its natural isotopic abundance.

15. The compound of claim 3, wherein the compound is:

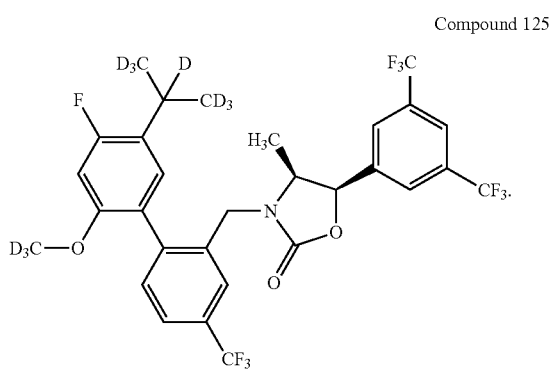 [SMILES: [2H]C([2H])([2H])Oc1cc(F)c(C([2H])(C([2H])([2H])[2H])C([2H])([2H])[2H])cc1-c1ccc(C(F)(F)F)cc1CN1C(=O)O[C@H](c2cc(C(F)(F)F)cc(C(F)(F)F)c2)[C@@H]1C]

Compound 125

* * * * *